US008734865B2

(12) United States Patent
Choulot et al.

(10) Patent No.: US 8,734,865 B2
(45) Date of Patent: May 27, 2014

(54) LUPIN TOTAL EXTRACT CONSISTING OF A LUPIN SUGAR EXTRACT AND A LUPIN PEPTIDE EXTRACT, METHOD FOR THE PRODUCTION AND USE THEREOF

(75) Inventors: Jean-Christophe Choulot, Rambouillet (FR); Antoine Piccirilli, Villennes/Seine (FR); Nathalie Piccardi, Arceau (FR); Philippe Msika, Versailles (FR); François Paul, Toulouse (FR)

(73) Assignee: Laboratoires Expanscience, Coubevoie (FR)

( * ) Notice: Subject to any disclaimer, the term of this patent is extended or adjusted under 35 U.S.C. 154(b) by 908 days.

(21) Appl. No.: 11/547,031

(22) PCT Filed: Apr. 4, 2005

(86) PCT No.: PCT/FR2005/000810
§ 371 (c)(1),
(2), (4) Date: Feb. 6, 2007

(87) PCT Pub. No.: WO2005/102259
PCT Pub. Date: Nov. 3, 2005

(65) Prior Publication Data
US 2008/0050458 A1  Feb. 28, 2008

(30) Foreign Application Priority Data
Apr. 8, 2004 (FR) ..................................... 04 03693

(51) Int. Cl.
| A61K 36/48 | (2006.01) |
|---|---|
| A61Q 5/02 | (2006.01) |
| A61K 31/715 | (2006.01) |
| A61K 8/97 | (2006.01) |
| A61K 36/00 | (2006.01) |

(52) U.S. Cl.
USPC ................ 424/757; 514/1.1; 514/23; 514/54; 424/70.13; 424/725

(58) Field of Classification Search
None
See application file for complete search history.

(56) References Cited

U.S. PATENT DOCUMENTS

| 2003/0045505 A1 * | 3/2003 | Martinez et al. ................. 514/61 |
| 2003/0157200 A1 | 8/2003 | Bonte et al. |

FOREIGN PATENT DOCUMENTS

| FR | 2 731 351 A1 | 9/1996 |
|---|---|---|
| FR | 2 778 102 A1 | 11/1999 |
| FR | 2 778 565 A1 | 11/1999 |
| FR | 2834638 | * 7/2003 |
| FR | 2834638 A1 | * 7/2003 |
| WO | WO 00/62789 A1 | 10/2000 |

OTHER PUBLICATIONS

Muzquiz et al. Lupin As a Potential Source of Raffinose Family Oligosaccharides: Preparative Method for Their Isolation and Purification. Industrial Crops and Products. 19 (1999) 183-188.*
Muzquiz et al. Lupins As a Potential Source of Raffinose Family Oligosaccharides: Preparative Method for Their Isolation and Purification. INdustrial Crops and Products. 1999. pp. 183-188.*
Lupin. retrieved from the internet <http://en.wikipedia.org/wiki/lupin>. Retrieved on Oct. 28, 2008.*
Kishi. Endoscopic Characteristics of the Healing Process of Ulcerative Colitis. Diagnostic and Therapeutic Endoscopy. vol. 5, pp. 37-48.*
Inflammation. retrieved from the internet. <http://en.wikipedia.org/wiki/Inflammation>. Retrieved on Oct. 29, 2008.*
Mohamed et al., "Composition of Lupinus albus," Database Biosis Online! Bioscienses Information Service, 1995, XP002308626, Database accession No. PREV199598592407 (abstract of Cereal Chemistry, vol. 72, No. 6, 1995, pp. 643-647).
Piotrowicz-Cieslak Agnieszka et al., "Cyclitols, galactosyl cyclitols and raffinose family oligosaccharides in Mexican wild lupin seeds," Database biosis Online! Biosciences Information Service, 2003, XP002308627, Database accession No. PREV200300352272 (abstract of Acta Societatis Botanicorum Poloniae, vol. 72, No. 2, 2003, pp. 109-114).
Gulewicz et al., "Biological activity of alpha-galactoside preparations from Lupinus angustifolius L. and Pisum sativum L. seeds," PubMed (abstract of J. Agric. Food Chem., Jan. 16, 2002; 50(2):384-9.

* cited by examiner

*Primary Examiner* — Chris R Tate
*Assistant Examiner* — Deborah Davis
(74) *Attorney, Agent, or Firm* — Foley & Lardner LLP

(57) ABSTRACT

The invention relates to a composition comprising a lupin total extract consisting of a lupin sugar extract, comprising at least 50% galactooligosaccharides by weight, in relation to the weight of dry matter, and a lupin peptide extract. The composition can also contain a chromane derivative or a chromene derivative. The invention also relates to a pharmaceutical and/or cosmetic composition comprising said lupin total extract, used advantageously as an anti-inflammatory agent, which repairs the cutaneous barrier and heals, used particularly in the prevention and/or treatment of erythemas.

18 Claims, 2 Drawing Sheets

LUPIN TOTAL EXTRACT CONSISTING OF A LUPIN SUGAR EXTRACT AND A LUPIN PEPTIDE EXTRACT, METHOD FOR THE PRODUCTION AND USE THEREOF

This application is a National Stage application of PCT/FR2005/000810, filed Apr. 4, 2005, which claims priority from French patent application FR 0403693, filed Apr. 8, 2004. The entire contents of each of the aforementioned applications are incorporated herein by reference.

The present invention relates to a composition comprising an extract of lupin sugars, enriched with galacto-oligo saccharides, and a peptide lupin extract. This composition may be used as an anti-inflammatory agent, which repairs the cutaneous barrier and heals, in particular in the prevention and/or treatment of erythemas with or without disruption of the cutaneous barrier.

Diaper rash is one of the most frequent dermatological disorders in infants. More than 50% of infants are affected, with a frequency of 25% during the first four weeks of life and an incidence peak between 9 and 12 months. The irritations are due to damages of the stratum corneum of the epidermis of the bottom of the infant, which have a dual origin:
- activation of urinary and fecal enzymes by maceration under the diapers,
- abrasive effect due to friction of the diapers on the skin.

In babies, urine is only a minor irritant of the skin. Investigations carried out in breast-fed infants have shown that the irritation was essentially due to lipases, proteases and ureases, contained in the stools, the latter enzymes being less active in breast-fed infants than those found in bottle-fed infants.

The pH of the stools of the babies is more acid, because of gastric microfluora which produces more metabolic acid. A higher pH, found in the stools of breast-fed babies, activates fecal enzymes which are then more aggressive for the skin. It was demonstrated by heating the stools that skin irritation is actually due to the fecal enzymes: the latter stools are then non-irritating on the skin of the animal; the irritating character is restored by adding trypsin and pancreatic lipase to these stools.

Further, fecal lipases facilitate proteolytic attack of the skin and increase its permeability to biliary salts. However lipases have proved to be non-irritating by themselves in investigations carried out in animals.

The increase in pH is therefore determining in the physiopathology of diaper rash. The combination stools-urine is what seems to be the most damageable. Indeed, urea contained in urines is degraded into ammonia by fecal urease. The formed ammonia causes alkalinization of the pH, which thereby potentializes the action of fecal enzymes.

Thus, formation of ammonia upon degradation of urea by the urease plays a significant role in sweating and diaper rash. In the particular case of diaper rash, formation of ammonia is not the direct cause of erythema but causes an increase in pH which promotes an increase in the activity of fecal lipases and proteases, thereby causing irritation at the skin.

Certain anti-urease agents against diaper rash and as a deodorant are already known, for example hydroxamic and hydroximic acids. More generally, the anti-urease activity of polyhydroxyphenols and quinones is also known.

The use of condensed tannins of carob and derivatives of chlorogenic acid in anti-urease cosmetic or dermatological compositions is also known. The condensed tannins used may be a hamamelis extract.

Finally, French Patent Application FR 2 778 102 describes the use of procyanodolic and anthocyanosides as anti-urease agents.

Regarding lupin, International Patent Application WO 00/62789 describes the use of a lupin peptide extract in inhibiting metalloproteases. This application thus describes the use of lupin peptide extract in a composition intended for treating arthrosis, parodontal diseases, skin lesions, inflammatory diseases as well as diseases related to lack of healing, to attack of dental enamel, tumoral or pathological angiogenesis. This patent application also describes the use of such a lupin peptide extract for treating skin lesions due to intrinsic aging of the skin, to aging under the action of solar radiation, to deleterious effects of tobacco, pollution and stress.

The publication of Piotr Gulewicz et al., "Biological Activity of α-galactoside Preparations from *Lupinus angustifolius* L. and *Pisum sativum* L. Seeds", J. Agric. Food Chem. Jan. 16, 2002, 50(2): 384-9, describes a lupin extract enriched with galacto-oligosaccharides and sucroses. This publication teaches that lupin galacto-oligosaccharides are not cytotoxic and they allow the number and biomass of bifidobacteria to be increased.

Patent Application EP 1 361 854 describes that photoprotective activities, notably anti-erythemal, anti-oxidant, anti-radical, anti-inflammatory, and vasculotropic activities of flavonoid type compounds, such as genistein, significantly increase when said compound is solubilized beforehand in a suitable solvent such as polyethylene glycols, polypropylene glycols, their derivatives, fatty alcohols, and ethoxylated polyols, and mixtures thereof. The compositions described in this application are particularly intended for preparing a drug capable of reducing and/or preventing erythemas, in particular actinic erythemas induced by UVA and/or UVB irradiations.

In spite of all these anti-urease compositions proposed in the prior art, there remains a need for new compositions for treating erythemas, in particular diaper rash.

Surprisingly, the inventors discovered that a composition comprising a total lupin extract, i.e., an extract of lupin sugars enriched with galacto-oligosaccharides and a lupin peptide extract, may be used for preventing and/or treating skin inflammation and/or lesions of the skin barrier, in particular erythemas.

Surprisingly, the inventors discovered that a composition comprising a total lupin extract is more effective, notably as an anti-inflammatory agent, than a composition comprising an extract of lupin sugars enriched with galacto-oligosaccharides alone or than a composition comprising a lupin peptide extract alone. There is therefore a synergistic effect between lupin sugars and peptides.

Thus, the object of the present invention is a composition comprising a total lupin extract consisting of an extract of lupin sugars, which comprises at least 50% by weight, relatively to the total weight of dry material, of galacto-oligosaccharides, and of a lupin peptide extract.

Galacto-oligosaccharides are oligosaccharides with a polymerization degree between 3 and 10, comprising galactose units.

Lupin combines significant protein contents (40% by weight on average) and oil contents (9-20% by weight) comparable with those of soya bean. Among the many varieties of lupin, soft white lupin (*lupinus albus*) provides the best compromise between composition and bitterness since, as opposed to Andean lupin, soft white lupin is practically depleted in alkaloids.

Soft white lupin comprises about 38-45% by weight of proteins. Main amino acids present in the protein fraction of white lupin are glutamine (20% by weight), asparagine and arginine (15 and 10% by weight, respectively). However, lupin is short in tryptophane and in sulphur-containing amino acids such as methionine, cystine, and cysteine.

White lupin comprises about 29 to 30% by weight of carbohydrates. The glucidic fraction of white lupin consists of stachyose which is the main sugar (about 55% by weight), followed by saccharose (about 25% by weight), verbascose (about 10% by weight) and raffinose (about 10% by weight). The majority of the present sugars consist of galacto-oligosaccharides.

Finally, lupin comprises about 6 to 17% by weight of lipids, which appear as limpid oil, the yellow orange colour of which is ascribed to the presence of provitamin A (carotenes). This oil is strongly unsaturated and it comprises essential fatty acids of the Omega 3, 6 and 9 type, oleic acid, linoleic acid and α-linolenic acid, respectively.

In the scope of the present invention, the extract of lupin sugars is an extract enriched with galacto-oligosaccharides.

According to an advantageous alternative of the invention, the lupin sugar extract advantageously comprises 55 to 90% by weight, more advantageously 57 to 85% by weight, still more advantageously 60 to 80% by weight, and further more advantageously 65 to 75% by weight, relatively to the weight of dry material of said extract of sugars, of galacto-oligosaccharides.

Galacto-oligosaccharides are advantageously selected in the group formed by verbascose, stachyose and raffinose.

Verbascose is a $C_{30}H_{52}O_{26}$ sugar, corresponding to the following formula:

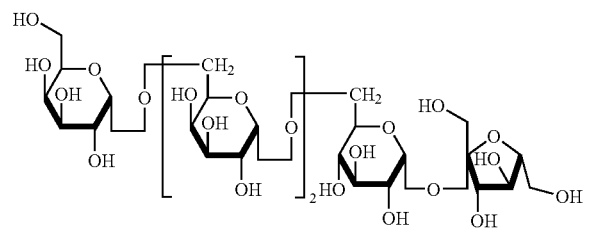

Raffinose is $C_{18}BH_{32}O_{16}$ sugar, corresponding to the following formula:

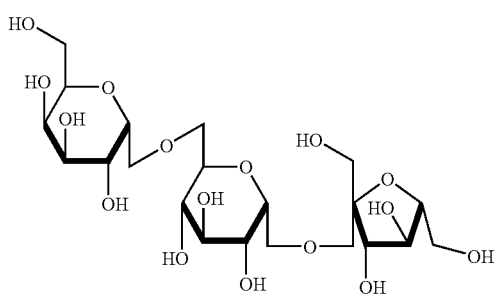

Stachyose is a $C_{25}H_{44}O_{21}$ sugar, of the following general formula:

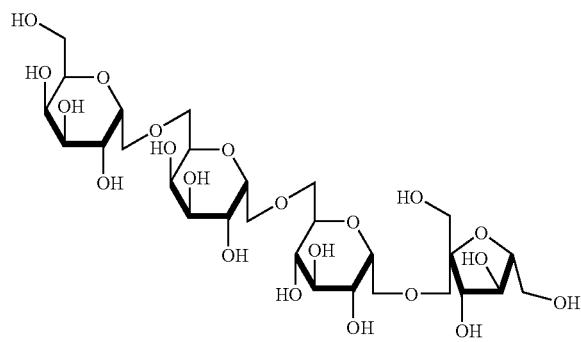

Thus, stachyose, for example, corresponds to a chaining of galactose-galactose-glucose-fructose, wherein the bond between galactose-galactose and galactose-glucose may be broken by means of a hydrolytic enzyme, α-galactosidase, and the bond between glucose and fructose may be broken by means of a hydrolytic enzyme, saccharase.

According to an advantageous alternative of the invention, the lupin sugar extract is capable of being obtained by a method comprising the following steps:
  a) extraction of lipids from lupin seed by means of a suitable solvent and recovery of the protein and saccharide fractions of lupin; and then
  b) from the fraction recovered in step a), separation of the fraction comprising the lupin sugars by ultrafiltration and recovery of said saccharide fraction; and
  c) if necessary, physical refining of the fraction comprising the lupin sugars, recovered subsequently to step b);
  d) obtaining subsequently to step b) or c), an extract of lupin sugars, very enriched in galacto-oligosaccharides.

The lipids from the lupin seeds are advantageously extracted during step a), by means of a solvent recognized as a non-toxic food solvent, notably by means of ethanol.

Ultrafiltration is a separation method in the liquid phase by permeation through semi-permeable membranes under the action of a pressure gradient, well-known to one skilled in the art.

During the ultrafiltration step, the cut-off threshold of the membranes is advantageously of 10,000 Daltons.

If necessary, the fraction comprising the lupin sugars, obtained subsequently to step b), is physically refined in order to obtain a colorless and perfectly demineralized solution, highly enriched in galacto-oligosaccharides.

Within the scope of the present invention, the lupin peptide extract comprises at least 50%, advantageously at least 70%, preferably at least 80% by weight of peptides, based on the total weight of the peptide extract. The peptide extract may notably be the lupin peptide extract described by the inventors in International Patent Application WO 00/62789.

The lupin peptide extract according to the invention is advantageously able to be obtained by a method comprising the following steps:
  i) extraction of the lipids from the lupin seed by means of a suitable solvent and recovery of the protein and saccharide fractions of the lupin;
  ii) extraction of the protein fraction by ultrafiltration and recovery of said protein fraction;
  iii) enzymatic hydrolysis of the protein, recovered subsequently to step ii), into peptides; and
  iv) purification by ultrafiltration of the peptides obtained subsequently to step iii);

v) concentration of the obtained extract subsequently to step iv) by partial or total evaporation of the water and recovery of the peptide extract.

The suitable solvent used in step i) is advantageously selected from the group of non-toxic food solvents, notably ethanol.

According to an advantageous alternative of the invention, the lupin peptide extract has the amino acid composition given in the following Table 1 (weight percent based on the total weight of amino acids):

TABLE 1

| Amino acids | Weight % based on the total amino acid weight |
|---|---|
| ASP | 11.3 |
| GLU | 23.2 |
| SER | 5.1 |
| HIS | 1.7 |
| GLY | 3.4 |
| THR | 3.2 |
| ALA | 2.8 |
| ARG | 10.3 |
| TIR | 6.1 |
| CYS-CYS | 2.4 |
| VAL | 3.8 |
| MET | 0.2 |
| PHE | 16.0 |
| ILE | 3.3 |
| LEU | 7.9 |
| LYS | 3.7 |
| PRO | 4.4 |

According to an advantageous alternative of the invention, in the total lupin extract (lupin sugars and peptides), the mass ratio between the dry material of the lupin sugar extract and the dry material of the lupin peptide extract is between 1 and 10, advantageously between 1.5 and 5, even more advantageously between 2 and 3, and preferably this ratio is about 2.5.

According to an advantageous alternative of the invention, in the total lupin extract (lupin sugars and peptides), the mass ratio between the galacto-oligosaccharides and the lupin peptides is between 1 and 10, advantageously between 1.5 and 5, even more advantageously between 2 and 3, and preferably this ratio is about 2.5. In the original lupin seed, the mass ratio between the galacto-oligosaccharides and the peptides is about 0.75.

Thus, within the scope of the present invention, the total lupin extract comprises 25 to 80% by weight of galacto-oligosaccharides, based on the weight of the dry material of said total extract, advantageously 30 to 75% by weight of galacto-oligosaccharides, even more advantageously 33 to 68% by weight of galacto-oligosaccharides, even more advantageously 40 to 60% by weight of galacto-oligosaccharides, even more advantageously 43 to 53% by weight of galacto-oligosaccharides, even more advantageously 45 to 51% by weight of galacto-oligosaccharides, based on the weight of the dry material of the total lupin extract.

Within the scope of the present invention, the lupin is advantageously selected from the group formed by the varieties *lupinus angustifolius, lupinus albus, lupinus luteus, lupinus mutabilis*, preferably lupin is of the *lupinus albus* genus. As an example of lupin of the soft white lupin genus (*lupinus albus*), the variety Ares which has a low alkaloid content, may notably be mentioned.

The composition according to the invention may further comprise, optionally, a chromane or chromene derivative described by the general formula (I).

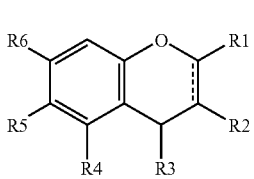

wherein:
the dotted line represents an additional bond or a lack of additional bond;
$R_1$ represents a hydrogen, a hydroxy, a methoxy, a phenyl, a phenyl substituted with 1, 2 or 3 hydroxy groups, a phenyl substituted with 1, 2 or 3 methoxy groups or a phenyl substituted with a flavone of formula:

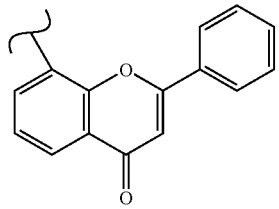 [SMILES: Cc1cccc2c(=O)cc(-c3ccccc3)oc12]

$R_2$ represents a hydrogen, a hydroxy, a methoxy, a phenyl, a phenyl, a phenyl substituted with 1, 2 or 3 hydroxy groups, or a phenyl substituted with 1, 2 or 3 methoxy groups or else, $R_1$ and $R_2$ together form a benzene ring;
$R_3$ represents a hydrogen, a hydroxy, or an oxo;
$R_4$, $R_5$ and $R_6$ either identical or different, represent a hydrogen, a hydroxy, a methoxy, a phenyl, a phenyl substituted with 1, 2 or 3 hydroxy groups, or a phenyl substituted with 1, 2 or 3 methoxy groups.

In a particular embodiment of the present invention, the chromane or chromene derivative is selected from the group formed by chromones, xanthones, and flavonoids. According to the present invention, the chromane or chromene derivative is advantageously a flavonoid.

The term of "flavonoid" in the sense of the present invention, means compounds comprising two aromatic cycles bonded together through three carbon atoms which form like an oxygenated heterocycle. According to the present invention, the flavonoid is advantageously selected from the group formed by flavones, flavonols, dihydro-2,3-flavonols, flavanones, flavanols, flavanediols, isoflavonoids and biflavonoids.

The term of "flavanol" in the sense of the present invention, means hydroxy-3-flavanes or hydroxy-4-flavanes.

The term of "flavane" in the sense of the present invention, means compounds of formula:

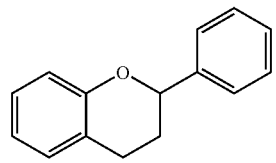 [SMILES: c1ccc(C2CCc3ccccc3O2)cc1]

The term of "flavanediol" in the sense of the present invention, means dihydroxy-3,4-flavanes.

The term of "isoflavonoid" in the sense of the present invention means isoflavones, as well as isoflavones with a structural formula, 3-phenyl-4-oxo-dihydro-2,3-chromenes.

The term of "bivaflonoid" in the sense of the present invention, means compounds of formula:

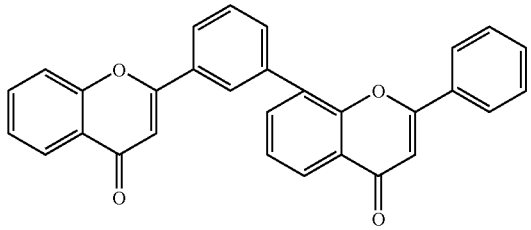 [SMILES: O=c1cc(-c2cccc(-c3cccc4c(=O)cc(-c5ccccc5)oc34)c2)oc2ccccc12]

According to the present invention, the flavonoid is advantageously an isoflavone or a mixture of isoflavones. The isoflavones which may be used according to the present invention are obtained by chemical synthesis or are natural substances extracted from natural products, notably from plants. Aglycone forms, isoflavones and glycosylated forms of the latter are distinguished. These different forms are illustrated by the following formulae.

Aglycone forms with formula:

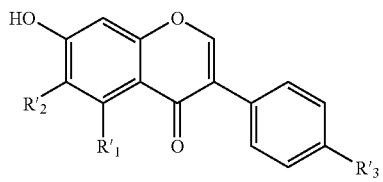

wherein $R'_1$ represents a hydrogen or a hydroxy, $R'_2$ represents a hydrogen or a methoxy and $R'_3$ represents a hydroxy.

Advantageously, according to the present invention, $R'_1$, $R'_2$ and $R'_3$ represent:

| $R'_1$ | $R'_2$ | $R'_3$ | Name of the compound |
|---|---|---|---|
| H | H | OH | Daidzein |
| OH | H | OH | Genistein |
| H | OCH$_3$ | OH | Glycitein |

Glycosylated forms with formula:

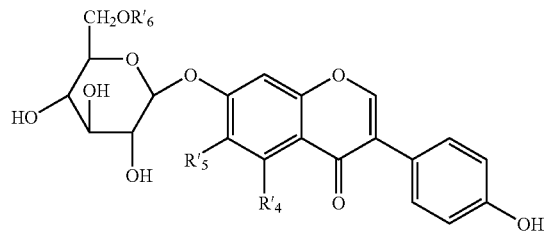

wherein $R'_4$ represents a hydrogen or a hydroxy, $R'_5$ represents a hydrogen or a methoxy and $R'_6$ represents a hydrogen.

Advantageously, according to the present invention, $R'_4$, $R'_5$ and $R'_6$ represent:

| $R'_4$ | $R'_5$ | $R'_6$ | Name of the compound |
|---|---|---|---|
| H | H | H | Daidzin |
| OH | H | H | Genistin |
| H | OCH$_3$ | H | Glycitin |

The glycosylated forms of isoflavones are the most abundant in nature. However, aglycone isoflavones have biological activities significantly superior to those of their glycosylated homologs. This is the case of natural isoflavones such as genistein, diadzein or glycitein.

Isoflavone according to the present invention is advantageously selected from the group formed by genistein, daidzein and glycitein, advantageously the flavonoid is genistein. In particular, the genistein which may be used according to the present invention is a product of plant origin with a titer from 85 to 90% by weight.

The object of the present invention is also a cosmetic and/or pharmaceutical composition comprising a composition as defined earlier, i.e., comprising a total lupin extract, (lupin sugar extract and lupin peptide extract), and additionally, optionally, a chromane or chromene derivative.

The cosmetic and/or pharmaceutical composition is advantageously intended for topical external use, moreover it may contain a cosmetically and/or pharmaceutically acceptable carrier.

The cosmetic and/or pharmaceutical composition which is advantageously applied according to the present invention may appear under all the dosage forms usually used for a topical external application. According to the present invention, the composition advantageously appears as a aqueous, hydroalcoholic or oily solution, an oil-in-water or water-in-oil emulsion, or a multiple emulsion, an aqueous or oily gel, a liquid, slurry or solid anhydrous product, or an oil dispersion in an aqueous phase by means of spherules, the spherules may be polymer nanoparticles, such as nanospheres and nanocapsules, or lipid vesicles of the ionic and/or non-ionic type. The cosmetic composition may be more or less fluid, may appear as a white or colored cream, a pomade, a milk, a lotion, an ointment, a serum, a slurry, a foam, an aerosol, or a stick.

The cosmetic and/or pharmaceutical composition applied according to the present invention may moreover contain the usual adjuvants in the cosmetic and/or pharmaceutical field, such as hydrophilic or lipophilic gelling agents, hydrophilic or lipophilic actives, preservatives, anti-oxidants, solvents, perfumes, fillers, chemical or mineral filters, pigments, chelating agents, smell absorbers, thermal waters, and coloring materials. The amounts of these different adjuvants are those conventionally used in cosmetics and/or pharmaceutics, and for example are from 0.01% to 20% by weight, based on the total weight of the cosmetic and/or pharmaceutical compositions. These adjuvants, depending on their nature, may be introduced into the fatty phase, into the aqueous phase, into the lipid vesicles, and/or into the nanoparticles.

When the composition according to the present invention is an emulsion, the proportion of the fatty phase may range from 5% to 80% by weight, preferably from 5% to 50% by weight, based on the total weight of the cosmetic and/or pharmaceutical composition. The oils, emulsifiers, and co-emulsifiers used in the cosmetic and/or pharmaceutical composition as an emulsion are selected from those conventionally used in their relevant field. The emulsifier and co-emulsifier are present in the composition in a proportion ranging from 0.3% to 30% by weight, preferably from 0.5% to 20% by weight, based on the total weight of the cosmetic composition.

Among the oils which may be used according to the present invention, mineral oils, other oils of vegetable origin (apricot oil, sunflower oil, plum oil), oils of animal origin, synthetic oils, silicone oils and fluorinated oils (perfluoropolyethers) may notably be mentioned. Fatty alcohols, such as cetyl alcohol, fatty acids or waxes, such as beeswax, may also be used as fatty materials according to the present invention.

Among the emulsifiers and co-emulsifiers which may be used according to the present invention, fatty acid and polyethylene glycol esters may notably be mentioned, such as PEG-40 stearate or PEG-100 stearate, fatty acid and polyol esters, such as glycerol stearate and sorbitan tristearate.

Among the hydrophilic gelling agents which may be used according to the present invention, carboxyvinyl polymers (carbomer), acrylic copolymers such as acrylate-alkylacrylate copolymers, polyacrylamides, polysaccharides, natural gums, and clays may notably be mentioned. Among the lipophilic gelling agents, modified clays such as bentones, fatty acid metal salts, hydrophobic silica and polyethylenes, may notably be mentioned.

The cosmetic and/or pharmaceutical compositions according to the invention may also be formulated as body hygiene products, notably intimate hygiene products. In a non-limiting way, anti-sweat products, deodorants as a spray or gel, shampoos, notably anti-dandruff shampoos, soaps, and dental hygiene products may be mentioned.

The object of the present invention is also the use of a composition comprising a lupin sugar extract, which comprises at least 50% by weight based on the total weight of dry material, advantageously from 55 to 90% by weight, even more advantageously from 57 to 85% by weight, even more advantageously from 60 to 80% by weight and even more advantageously from 65 to 75% by weight, based on the total weight of dry material, of galacto-oligosaccharides as an anti-inflammatory agent.

Indeed, the inventors have discovered that the lupin sugar extract according to the present invention has an anti-inflammatory action. It may therefore be used in making a drug, notably intended for treating or preventing allergic, inflammatory and/or irritating reactions or pathologies of the skin and/or of the mucosae. In particular, inflammatory pathologies, may be inflammatory dermatoses such as psoriasis, irritating dermites, auto-immune diseases, photo-immunosuppression, or graft rejection. "Photo-immunosuppression" in the sense of the present invention is meant to designate a reduction of the immune response induced by solar ultraviolet rays, and more particularly by ultraviolet B rays.

According to one embodiment of the present invention, the drug comprising a lupin sugar extract is intended for treating and preventing sensitive, reactive, uncomfortable, intolerant skins and/or mucosae, having a disorder of the skin barrier and/or having an immunological disequilibrium related to intrinsic, extrinsic (sun, pollution) or hormonal aging.

According to another alternative of the invention, the lupin sugar extract is also used for reducing the allergizing and/or irritating character of a composition such as a pharmaceutical preparation, a cosmetic preparation or a perfume. By allergizing character is meant the potential of certain compounds contained in said composition of behaving as allergens, i.e., compounds capable of inducing an immediate hypersensitivity and/or inflammatory reaction.

The present invention also relates to a cosmetic treatment method for sensitive, irritating, intolerant, allergy-prone, aged, skins and/or mucosae with a disorder of the skin barrier, with skin erythemas, or having a disorder or a non-pathological immunological disequilibrium related to intrinsic, extrinsic or hormonal aging, characterized in that it consists of applying on the skin and/or on the mucosae, a lupin sugar extract of a cosmetic composition comprising said extract.

The present invention also relates to the use of a composition comprising a total lupin extract (lupin sugar extract and lupin peptide extract, and further optionally, a chromane or chromene derivative for making a drug. The drug is notably intended for preventing and/or treating erythemas, in particular diaper rashes or solar erythemas, rosacea, as well as any cutaneous inflammation consecutive:
  i) to an external aggression; and/or
  ii) to dysfunction of the metabolism or of the structure of the skin.

Within the scope of the present invention, by the expression "dysfunction of the metabolism or of the structure of the skin", the term "skin" representing the keratinized skin or oral, gingival, nasal or vaginal mucosae, is meant all the aggressions, disequilibria, anomalies of the skin barrier, causing discomfort or a pathology, which may be worsened by an external event or endogenous factors: dryness, ichtyosis, ulcers . . . ; also said expression means all the inflammatory skin diseases causing or centered on a degraded skin barrier: atopy, psoriasis, seborrheic dermitis, acne, erythro-rosacea or rosacea, as well as diseases or dysfunctions paving the way for either pathogenic or non-pathogenic germs, or caused by the latter. This list of pathologies has no limiting character as very often alteration of the barrier, inflammation and bacterial or fungic proliferation, are related.

Within the scope of the present invention, the external aggression may be an aggression induced by UVA and/or UVB irradiations. In the case of solar erythema, the cosmetic compositions or the drugs according to the present invention are directly applied on the skin before and/or during and/or after exposure to the sun, advantageously after appearance of erythema on the skin. The external aggression may also be all weather aggressions (cold, wind) and any contact with an irritating agent, a chemical or natural allergen, or a rubefacient agent. This may also be repetitive frictions of the diapers of the infants, of the women or of the elderly persons, but may also be consecutive to a medical or surgical treatment act (laser, peeling, electric hair-removal, electrocoagulation). Also, maceration of folds and armpits or mucosae optimizes by occlusion, proliferation of the germs and inflammation.

The composition according to the invention, comprising a total lupin extract, has a triple anti-enzymatic activity, i.e., combined anti-protease activity, anti-lipase activity and anti-urease activity.

Thus, the composition according to the invention may be used for making a drug intended for preventing and/or treating allergic, inflammatory and/or irritating reactions or pathologies of the skin and/or of the mucosae. The composition according to the invention may also be used as an agent for favoring healing.

The present invention also relates to a cosmetic treatment method for sensitive, irritated, intolerant, allergy-prone, aged, skins and/or mucosae, having a disorder of the skin barrier, having cutaneous red spots or having a disorder or an immunological non-pathological disequilibrium related to intrinsic, extrinsic or hormonal aging, characterized in that it consists of applying on the skin and/or on the mucosae, a total lupin extract or a cosmetic composition comprising said extract.

The present invention also relates to a cosmetic treatment method for controlling the pH of the skin, characterized in that it consists of applying on the skin and/or the mucosae, a total lupin extract or a cosmetic composition comprising said extract.

Finally, the present invention relates to a cosmetic treatment method for repairing the surface condition of the skin, notably for repairing lesions of the skin barrier, characterized in that it consists of applying on the skin a total lupin extract or a cosmetic composition comprising said extract.
When the skin is subject i) to external aggression; and/or
ii) to dysfunction of its metabolism or its structure,
its surface may be altered and/or lesions of the skin barrier may be observed.

The following examples are given as non-limiting examples and illustrate the present invention.

EXAMPLE 1

Figure 1:
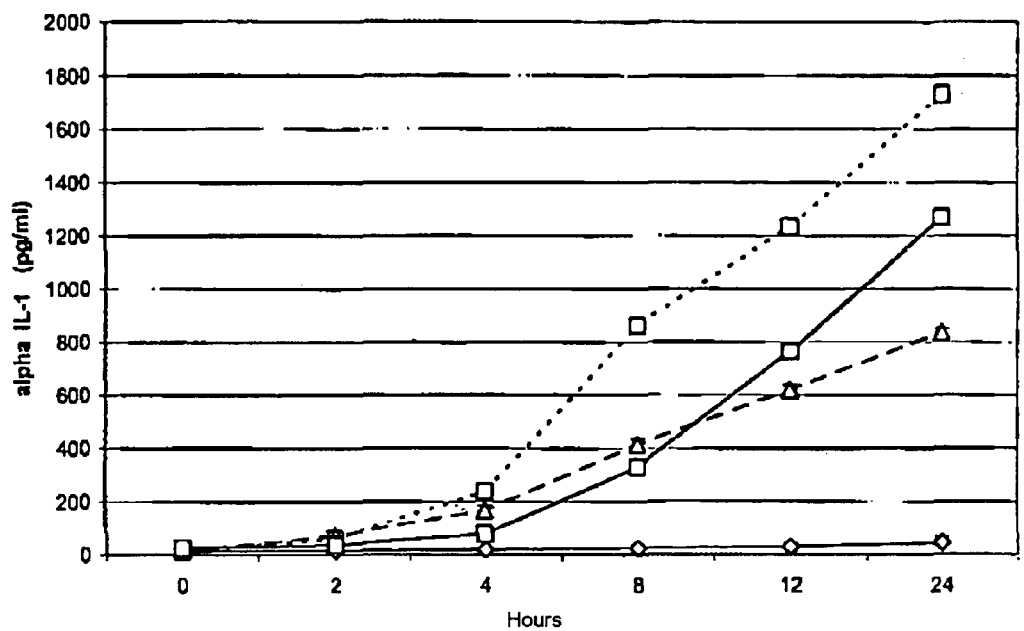
FIG. 1 illustrates the amount of IL-1α released by keratinocytes versus time (release kinetics).

Composition of a Total Lupin Extract According to the Invention

TABLE 2

| Composition criteria | |
|---|---|
| Aspect | Pale yellow colored aqueous solution |
| Dry material (DM) content | 35% |
| Total peptide content | 10% |
| % of α-aminated nitrogen (leucine/DM equivalent) | 5.5 |
| Lupin galacto-oligosaccharides content (CLHP/DM %) | 48% |
| pH | 6.5 |
| Absorbance at 420 nm | 0.420 |
| Absorbance at 550 nm | 0.024 |
| Preservative | 0.45% |

The dry matter (DM) consists of lupin peptides and sugars, thus the total lupin extract comprises 25% by weight of sugars, based on the total weight of the extract. Thus, in this total lupin extract, the ratio of lupin sugar extract over lupin peptide extract is 2.5. This total lupin extract comprises 48% by weight of galacto-oligosaccharides, based on the total weight of the dry matter of said total extract. Thus, the lupin sugar extract comprises 67.2% by weight of galacto-oligosaccharides, based on the total weight of the dry material of said sugar extract.

EXAMPLE 2

Method for Preparing a Total Lupin Extract According to the Invention

A) Method for Preparing a Lupin Sugar Extract
a) Delipidation with Ethanol
9.9 kg of lupin flour are mixed with 85 L of ethanol and this mixture is maintained under stirring for 1 hr at room temperature. The mixture is then left to decanter and then the alcoholic fraction is removed.

b) Recovery of the Saccharide Fraction:
i) Dispersion in Water and pH Adjustment
90 L of water are added to the decanted fraction and then the pH is adjusted to 8.5 with soda.
ii) Centrifugation and Filtration with a Plate Filter
The thereby obtained solution is centrifugated on a continuous decanter of the Westfalia type, and then filtered on a plate filter. The filtrate is collected.
iii) Ultrafiltration with a 10 kDa Cut-Off Threshold Membrane and Concentration
The filtrate is concentrated by a factor of 2. A diafiltration is then carried out with 2 volumes of demineralized water (i.e., 140 L of demineralized water) and the ultrafiltrate is recovered, which is then concentrated with a 200 Da cut-off threshold membrane (concentration factor equal to 8), i.e., a total volume of concentrated sugars of 15 L.
c) Physical Refining of the Saccharide Fraction:
i) Demineralization and Concentration
The obtained concentrated sugars pass through two columns of ion exchanger resins mounted in series (cation exchanger and anion exchanger, respectively) and are then concentrated by nanofiltration (membrane with a 200 Da cut-off threshold) Concentrated demineralized sugars are recovered (4 L with 17 g/L of sugars).
ii) Discoloration with Active Coal
0.1 kg of coal is added to 4 L of sugar solution. It is left to react for 1 hour at room temperature and then it is filtered with a plate filter.
iii) Final Concentration
The recovered filtrate is concentrated by nanofiltration with a 200 Da cut-off threshold membrane. Finally, 2.46 kg of 275 g/L sugar solution is obtained.

B) Method for Preparing a Lupin Peptide Extract
a) Extraction and Purification of Lupin Proteins
This step comprises aqueous solubilization of the soluble fraction at an alkaline pH followed by separation of the insolubles:
From delipidated and milled lupin cake, extraction of the proteins was carried out at pH 9.0 (a pH adjusted by adding soda) with a flour/water ratio equal to 1/10 (p/p). The solution is incubated under stirring at room temperature for 1 hour. The insoluble portion of the cake is then separated from the soluble portion by draining. The obtained cake is washed. The soluble fraction containing the soluble proteins and sugars are diafiltered on an ultrafiltration module with a cut-off threshold of 10,000 Daltons in order to separate the proteins (retentate) from the soluble sugars (ultrafiltrate).

b) Production and Purification of Peptides by Enzymatic Hydrolysis:
The ultrafiltration retentate containing the proteins is adjusted to a concentration of 100 g/l and then hydrolyzed at pH 8.0 in the presence of glucanase at 55° C. for about 3 hours. After hydrolysis, the enzyme is denaturated by heat treatment for 15 mins at 85° C. As soon as the solution has cooled down, it is neutralized by adding hydrochloric acid. The obtained peptides are purified by diafiltration on an ultrafiltration module with a cut-off threshold of 10,000 Daltons. The obtained solution is then nanofiltered in order to desalt (removal of sodium chloride) and to concentrate the peptide fraction. The solution of peptides is finally discolored by means of 3% active coal (1 hour at 50° C.), the coal is filtered off.
The concentrated solution to be dehydrated is then injected as a fine mist at the top of a tower simultaneously with a hot air draft. Finally, the powder is recovered, spray-dried and then conditioned.

C) Making the Total Lupin Extract

The lupin peptide extract, the lupin sugar extract and the preservative are mixed. Thus, under stirring, the following ingredients are mixed:
- 2.46 kg lupin sugars with 275 g/L of DM i.e., 0.676 kg of DM;
- 0.32 kg lupin peptide extract with 95% DM, i.e., 0.304 kg of DM; and
- 12.5 g of preservative (0.4% w/w).

One then has a lupin sugars DM/lupin peptide extract DM mass ratio of 2.22.

Next, homogenization under mechanical stirring is carried out followed by sterilizing microfiltration and conditioning:
- 2-step filtration: with a plate filter and then under sterile conditions with a sterilizing cartridge with a cut-off threshold of 0.2 μm;
- Conditioning Produced amount: 2.6 kg with 36.2% of DM.

The following Table 3 gives the composition of the total lupin extract prepared according to the method described above:

TABLE 3

| Aspect | Slight orange solution | |
|---|---|---|
| Analytical criteria | | |
| Dry material (DM) | 36.2% | |
| pH (¼ dilution) | 6.69 | |
| Absorbance at 420 nm | 0.6 | |
| Absorbance at 550 nm | 0.053 | |
| Composition of the dry material | | |
| α-aminated nitrogen | 5.1% w/w of DM | |
| | w/w % of total extract | w/w % of DM of total extract |
| Monosaccharides | 3.6 | 10 |
| Saccharose | 4 | 11 |
| Stachyose | 12.9 | 35.6 |
| Verbascose | 2 | 5.5 |
| Raffinose | 2.5 | 6.9 |
| Total of sugars | 25 | 69 |
| Total of galacto-oligosaccharides | 17.4 | 48 |

EXAMPLE 3

Formulation Intended for Treating and/or Preventing Diaper Rash

| | |
|---|---|
| Purified water | 56.6% |
| Zinc oxide | 10.0% |
| Caprylyl glycol | 5.0% |
| Fluid vaseline oil | 5.0% |
| Propylene glycol dioctanoate | 4.0% |
| Methyl glucose dioleate | 4.0% |
| Organophilic titanium oxide | 3.0% |
| Copolymer PEG-45/dodecyl glycol | 3.0% |
| Ceresin wax | 2.0% |
| Total lupin extract | 2.0% |
| Dextrogyral penthanol | 2.0% |
| 35% neutral vitamine F | 1.0% |
| Karite butter | 1.0% |
| Potassium sorbate | 0.5% |
| Methyl parahydroxybenzoate | 0.3% |
| Magnesium sulfate | 0.3% |
| Propyl parahydroxybenzoate | 0.2% |
| Genistein | 0.10% |

EXAMPLE 4

Formulation for an Intimate Hygiene Washing Cream

| Ingredients | % w/w |
|---|---|
| Water | QSP 100 |
| Coco-glucoside | 10.00 |
| Disodium lauryl sulphosuccinate | 2.00 |
| Sodium cocoyl isethionate | 2.00 |
| Corn starch | 2.00 |
| Cetearyl alcohol | 2.00 |
| Hydroxypropyl guar | 2.00 |
| Citric acid | QS pH |
| Total lupin extract | 0.1-10 |
| Genistein | 0.1-10 |
| Glycerin | 0.45 |
| Polyquaternium 10 | 0.30 |
| Tetrasodium EDTA (ethylene diamine tetraacetic acid) | 0.20 |
| Titanium dioxide | 0.10 |
| Preservative | QS |

EXAMPLE 5

Formulation for an Intimate Hygiene Foam

| Ingredients | % w/w |
|---|---|
| Water | QSP 100 |
| Sodium lauroamphoacetate | 10.00 |
| Coco-glucoside | 10.00 |
| Magnesium laureth sulfate | 5.00 |
| PEG-40 glycerol cocooate | 2.50 |
| PEG-150 distearate | 1.00 |
| Sodium coceth sulfate | 1.00 |
| Total lupin extract | 0.1-10 |
| Genistein | 0.1-10 |
| Citric acid | QS pH |
| Perfume | SA |
| Preservatives | QS |

EXAMPLE 6

Formulation Intended for Treating and/or Preventing Diaper Rash

| | |
|---|---|
| Purified water | 56.7% |
| Zinc oxide | 10.0% |
| Caprylyl glycol | 5.0% |
| Fluid vaseline oil | 5.0% |
| Propylene glycol dioctanoate | 4.0% |
| Methyl glucose dioleate | 4.0% |
| Organophilic titanium oxide | 3.0% |
| Copolymer PEG-45/dodecyl glycol | 3.0% |

-continued

| | |
|---|---|
| Ceresin wax | 2.0% |
| Total lupin extract | 2.0% |
| Dextrogyral penthanol | 2.0% |
| 35% neutral vitamin F | 1.0% |
| Karite butter | 1.0% |
| Potassium sorbate | 0.5% |
| Methyl parahydroxybenzoate | 0.3% |
| Magnesium sulfate | 0.3% |
| Propyl parahydroxybenzoate | 0.2% |

EXAMPLE 7

Anti-inflammatory Activity of Lupin Sugars

An inflammation was modeled in vitro by adding SDS (sodium dodecyl sulfate). SDS induces production of beta IL-1, a key mediator of the inflammatory reaction by keratinocytes. The produced amount of beta IL-1 by keratinocytes in response to SDS is therefore proportional to the intensity of the inflammatory response.

Cell cytotoxicity was evaluated beforehand (neutral red test) in order to determine non-toxic working dosages for the cells. Thus, the inhibiting concentration 50 $IC_{50}$ (the concentration which induces a mortality of 50% of the cells, relatively to the total number of cells) is about 10% of the lupin sugar extract at 24 hours and 48 hours.

The cells are pretreated for 24 hours with different concentrations of a lupin sugar extract solution (0.5%; 1% and 5%, i.e., 0.375%; 0.75% and 3.75% of galacto-oligosaccharides), and they are then placed in the presence of SDS (20 μg/mL) for 16 hours. The amount of beta IL-1 is dosed in culture media by an ELISA test (immunological dosage).

The following Table 4 shows the obtained results.

TABLE 4

| | Control cells | SDS | 0.5% of lupin sugar extract | 1% of lupin sugar extract | 5% of lupin sugar extract |
|---|---|---|---|---|---|
| beta IL-1 (pg/mL) | 0.26 | 10.42 | 5.25 | 6.33 | 3.83 |

Thus, lupin sugars reduce by 50-60% (for the strongest concentration used i.e. 5%) the production of beta IL-1 by keratinocytes subject to inflammatory stress. The lupin sugars therefore have a very significant anti-inflammatory activity.

EXAMPLE 8

Anti-inflammatory Activity of Total Lupin Extract (Lupin Sugars Enriched in Galacto-oligosaccharides and Lupin Peptides)

The experimental protocol is identical with that of Example 7. The results are expressed as a percentage of inhibition of beta IL-1 synthesis by treated cells (sugars+peptides+SDS) as compared with non-treated cells (SDS alone).

TABLE 5

| Percentage of galacto-oligosaccharides | 0.375 | 0.75 | 3.75 | 0 | 0.375 | 0.75 | 3.75 |
|---|---|---|---|---|---|---|---|
| Percentage of peptides | 0 | 0 | 0 | 0.01 | 0.01 | 0.01 | 0.01 |
| % of inhibition | 49 | 39 | 63 | 18 | 90 | 88.5 | 95 |

Lupin peptides alone therefore have moderate anti-inflammatory activity. Quite unexpectedly, when the lupin peptides and sugars are used simultaneously, anti-inflammatory activity of the sugars is potentialized, and vice-versa. The lupin sugars and peptides therefore act synergistically for inhibiting inflammation induced by SDS.

EXAMPLE 9

Anti-inflammatory Activity of a Composition Comprising a Total Lupin Extract (Lupin Sugars Enriched with Galacto-oligosaccharides and Lupin Peptides) and a Chromene or Chromane Derivative The exemplified formulation of Example 3 was tested.

An inflammation was modeled in vitro on a model of re-constructed epidermis (Skinethic®) exposed to the action of SLS (sodium lauryl sulfate). The amount of α IL-1, a major mediator of irritating and inflammatory phenomena, released by keratinocytes, was quantitated at several times (release kinetics).

The formulation was applied on epidermises either before adding SLS (evaluation of the preventive effect), or after adding SLS (evaluation of the curative effect).

SLS induces production of α IL-1 in a time-dependent way. During the first 8 hours, the tested formulation reduces by about 40% the production and/or the release of α IL-1, with a comparable preventive and curative efficiency.

Beyond 8 hours, the curative effect (50% inhibition) seems to be larger than the preventive effect (30% inhibition).

The enclosed FIG. 1 shows the results obtained (production of α IL-1 (pg/mL) versus time (hours)).

| Caption: | |
|---|---|
| —◇— | Control |
| ----□---- | SLS alone |
| ---△--- | SLS and the tested formula |
| —□— | Tested formula and then SLS |

In conclusion, this test demonstrates that the formulation may limit the inflammatory reaction induced by SLS in a reconstructed epidermis model. It action is both curative and preventive.

EXAMPLE 10

Figure 2:
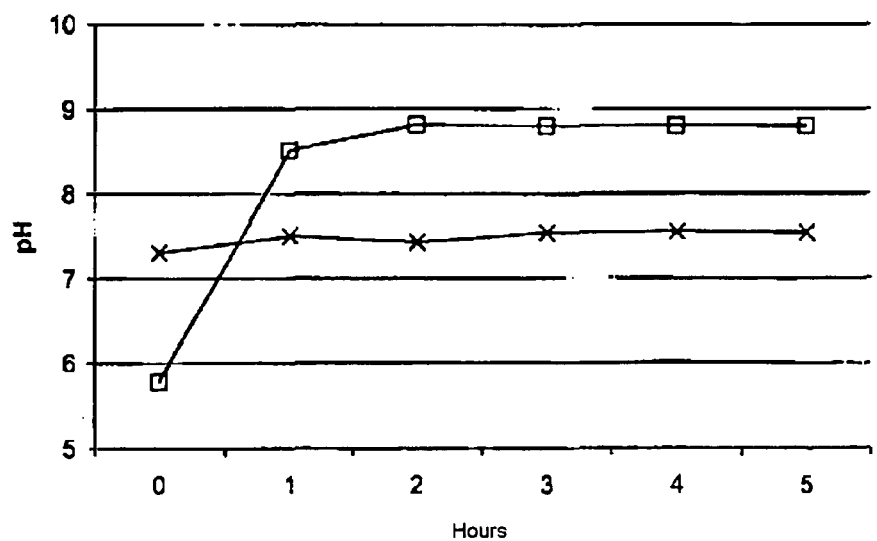
FIG. 2 illustrates the anti-urease activity of the exemplified formulation in Example 3, illustrated by the value of the pH versus time upon adding a urease solution.

Anti-urease Activity of a Composition Comprising a Total Lupin Extract (Lupin Sugars Enriched with Galacto-oligosaccharides and Lupin Peptides) and a Chromene or Chromane Derivative The formulation exemplified in Example 3 was tested. The protocol is based on measuring pH. The product to be tested in introduced into a vial, a pH=6 buffer is added and then a urea solution is added. A urease solution is then added and the pH of the aqueous phase is measured every hours. The urea will degrade into ammonia in the presence of urease and the pH will increase. An anti-urease activity will be expressed by stabilization of the pH. The enclosed FIG. 2 shows the results obtained (the pH versus time expressed in hours).

| Caption: | |
|---|---|
| —□— | Control |
| ----X---- | Formulation according to the invention |

The control corresponds to a urea and urease solution without any active product. Urease will degrade urea into ammonia.

The anti-urease activity of the finished product was able to be demonstrated by this test. Indeed, whereas the pH of the control solution increases, that of the one containing the formulation of Example 3 remains stable.

EXAMPLE 11

Anti-lipase Activity of a Composition Comprising a Total Lupin Extract (Lupin Sugars Enriched with Galacto-oligosaccharides and Lupin Peptides) and a Chromene or Chromane Derivative The anti-lipase activity of a solution containing, based on the total weight of the solution, 2% by weight of a total lupin extract according to the invention (lupin sugars enriched with galacto-oligosaccharides and lupin peptides, the mass ratio between the dry material of the lupin sugar extract and the dry material of the lupin peptide extract being 2.5) and 0.1% by weight of genistein was evaluated in tubo (biochemical model: lipase+substrate+test product).

Different dilutions were tested.

Figure 3:
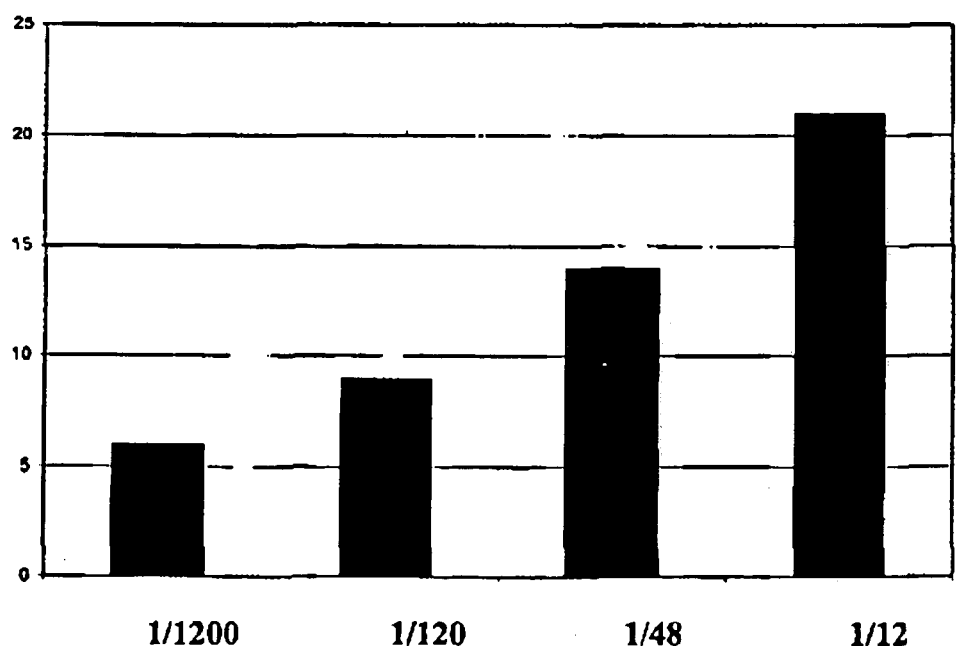
FIG. 3 illustrates the percentage of lipase activity inhibition as compared with a control for a more or less diluted tested solution. The given values (1/1200, 1/120, 1/48 and 1/12) correspond to the dilutions of the tested solution (v/v).

The enclosed FIG. 3 shows the results obtained (percentage of inhibition of the lipase activity as compared with the control, for different dilutions: 1/1200, 1/120, 1/48 and 1/12). The total lupin extract+genistein mixture has a highly significant anti-lipase activity. This activity is dose-dependent and effective for very low dilutions (from 1/1200 to 1/12).

EXAMPLE 12

Consumer Test Under Medical Control; Comparative Evaluation of 3 Cosmetic Products for the Care of Diaper Rash of Babies This investigation was carried out at pediatrician's and it included 127 children. The average age of the children was 10.6 months, 30% of them had a low intensity irritation of the bottom epidermis and 70% of them had moderate intensity irritation (88% with a dry irritation, 12% with oozing irritation).

After the first consultation, the physician prescribed one of the 2 creams of the protocol, unaware of its name: A=formulation of Example 3, B=formulation of Example 3 without any active ingredient, i.e., without any total lupin extract and without any isoflavone.

The creams were routinely applied after diaper change, for 10 to 30 days. At the end of each consultation on day 0, day 15 and day 30, the practitioner conducted a clinical examination and filled in a questionnaire. A questionnaire for self-evaluations was also proposed to the users (mothers).

The statistical analyses used a Khi2 test on the independence of each variable, Kruskal and Wallis, and Mann and Whitney non-parametric tests. The children were distributed in the following way: A: 87 tested infants, B: 40 tested infants.

a) Disappearance of the Irritations of the Bottom Epidermis

By applying after each diaper change, formulation A, total disappearance of the diaper rash was obtained after 4.9 days for 85% of the tested babies. By applying after each diaper change, formulation B, total disappearance of the diaper rash was obtained after 5.1 days for 73% of the tested babies. Formulation A thus obtained the highest percentage of total disappearance of the erythemas, disorders of the barrier and irritations of the bottom epidermis.

In the remaining populations, the development of the lesions was favorable but partial.

b) Results from the User Self-evaluation Questionnaires (Mothers)

The global performances of formulations A and B are indicated in Table No. 6. By comparing the performances of formulation A to those of formula B, it was possible to confirm its statistically significant superiority on the majority of the evaluated criteria.

TABLE NO. 6

| | Efficiency | |
|---|---|---|
| Evaluated criteria | A | A/B |
| The product calms irritations | 92% | S |
| Promotes repair of the lesions | 91% | S |
| Reduces recurrences of the erythema | 80% | S |
| Cosmetic approval | | |
| Thick and covering consistency | 97% | S |
| Holds on properly between two diaper changes | 94% | S |
| Suitable for care during baby diaper change | 94% | S |
| Level of satisfaction for the product | 94% | S |

S: Criteria where the reported difference between both products is statistically significative.

Conclusion: Rapid and total disappearance of the erythemas and lesions was obtained with formulation A within 4.9 days in 85% of the cases.

The invention claimed is:

1. A method for treating inflammatory reactions of the skin comprising the administration to a patient in need thereof of an effective amount of a composition comprising:
   at least 0.375% lupin sugar extract, which comprises at least 50% by weight, based on the weight of the dry material, of galacto-oligosaccharides,
   at least 0.01% lupin peptide extract wherein the lupin peptide extract comprises at least 50% by weight of peptides.

2. The method according to claim 1, wherein the sugar extract comprises 55-90% by weight of galacto-oligosaccharides, based on the weight of the dry material of the sugar extract.

3. The method according to claim 1, wherein the galacto-oligosaccharides are selected from the group formed by verbascose, stachyose and raffinose.

4. The method according to claim 1, wherein the sugar extract is obtained by a method comprising the following steps:
   a) extraction of lipids from the lupin seed by means of a suitable solvent and recovery of the protein and saccharide fractions of the lupin; and then
   b) from the fraction recovered in step a), separation of the fraction comprising the lupin sugars by ultrafiltration and recovery of said saccharide fraction; and
   c) if need be, physical refining of the fraction comprising the lupin sugars, recovered subsequently to step b);

d) obtaining subsequently to step b) or c), a lupin sugar extract, highly enriched in galacto-oligosaccharides.

5. The method according to claim 1, wherein the mass ratio between the galacto-oligosaccharides and the lupin peptides is between 1:1 and 10:1.

6. The method according to claim 1, wherein the mass ratio between the galacto-oligosaccharides and the lupin peptides is between 2:1 and 3:1.

7. The method according to claim 1, wherein the peptide extract comprises at least 50% of peptides.

8. The method according to claim 1, wherein the lupin peptide extract is obtained by a method comprising the following steps:
   ii) extraction of the lipids of lupin seed by means of a suitable solvent and recovery of the protein and saccharide fractions of the lupin;
   ii) extraction of the protein fraction by ultrafiltration and recovery of said protein fraction;
   iii) enzymatic hydrolysis of the proteins, recovered subsequently to step ii), into peptides; and
   iv) purification by ultrafiltration of the peptides obtained subsequently to step iii);
   v) concentration of the extract obtained subsequently to step iv), by partial or total evaporation of the water and recovery of the peptide extract.

9. The method according to claim 1, wherein the lupin is selected from the group formed by the varieties lupinus angustifolius, lupinus aibus, lupinus luteus, lupinus mutabilis.

10. The method according to claim 1, wherein the lupin is lupinus albus genus.

11. The method according to claim 1, wherein, the composition further comprises a chromane or chromene derivative described by the general formula (I)

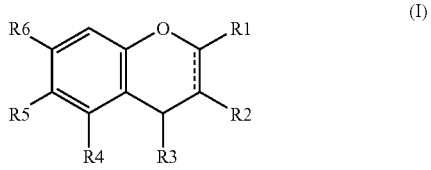

(I)

wherein:
the dotted line represents an additional bond or a lack of additional bond;

$R_1$ represents a hydrogen, a hydroxy, a methoxy, a phenyl, a phenyl substituted with 1, 2 or 3 hydroxy groups, a phenyl substituted with 1, 2 or 3 methoxy groups or a phenyl substituted with a flavone of formula:

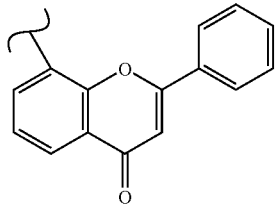 [SMILES: Cc1cccc2c(=O)cc(-c3ccccc3)oc12]

$R_2$ represents a hydrogen, a hydroxy, a methoxy, a phenyl, a phenyl, a phenyl substituted with 1, 2 or 3 hydroxy groups, or a phenyl substituted with 1, 2 or 3 methoxy groups or else, $R_1$ and $R_2$ together form a benzene ring;

$R_3$ represents a hydrogen, a hydroxy, or an oxo;

$R_4$, $R_5$ and $R_6$ either identical or different, represent a hydrogen, a hydroxy, a methoxy, a phenyl, a phenyl substituted with 1, 2 or 3 hydroxy groups, or a phenyl substituted with 1, 2 or 3 methoxy groups.

12. The method according to claim 11, wherein the chromane or chromene derivative is selected from the group formed by chromones, xanthones and flavonoids.

13. The method according to claim 12, wherein the chromane or chromene derivative is a flavonoid.

14. The method according to claim 13, wherein the flavonoid is selected from the group formed by flavones, flavonols, dihydro-2, 3-flavonols, flavanones, flavanols, flavanediols, isoflavanoids and biflavonoids.

15. The method according to claim 14, wherein the flavonoid is an isoflavone, or a mixture of isoflavones.

16. The method according to claim 15, wherein the isoflavone is selected in the group formed by genistein, daidzein and glycitein.

17. The method according to claim 1, wherein inflammatory reactions are a disease selected from the group consisting of erythemas, rosacea as well as any cutaneous inflammation consecutive i) to an external aggression and/or ii) to a dysfunction of the metabolism or the structure of the skin.

18. The method according to claim 1, wherein inflammatory reactions are diaper rashes or solar erythemas.

* * * * *